US005719324A

United States Patent [19]
Thundat et al.

[11] Patent Number: 5,719,324
[45] Date of Patent: Feb. 17, 1998

[54] MICROCANTILEVER SENSOR

[75] Inventors: Thomas G. Thundat, Knoxville; Eric A. Wachter, Oak Ridge, both of Tenn.

[73] Assignee: Lockheed Martin Energy Systems, Inc., Oak Ridge, Tenn.

[21] Appl. No.: 491,203

[22] Filed: Jun. 16, 1995

[51] Int. Cl.[6] .................................................. G01N 27/00
[52] U.S. Cl. ........................... 73/24.01; 73/24.06; 422/88
[58] Field of Search ................................ 73/24.01, 24.04, 73/24.06, 24.05; 422/88, 91, 83; 310/312, 321, 330, 331

[56] References Cited

U.S. PATENT DOCUMENTS

| | | | |
|---|---|---|---|
| 3,766,616 | 10/1973 | Staudte | 310/312 |
| 4,542,640 | 9/1985 | Clifford | 73/31.06 |
| 4,549,427 | 10/1985 | Kolesar, Jr. | 73/24.01 |
| 5,445,008 | 8/1995 | Wachter et al. | 73/24.06 |

OTHER PUBLICATIONS

Daniel Rugar, et al., "Atomic Force Microscopy", Physics Today, Oct. 1990, pp. 23–30.

J.K. Gimzewski, et al., "Observation of a chemical reaction using a micromechanical sensor", Chemical Physics Letters, vol. 217, No. 5, 6, Jan. 28, 1994, pp. 589–594.

J.R. Barnes, et al., "A femtojoule calorimeter using micromechanical sensors", Rev. Sci. Instrum. 65 (12) Dec. 1994, American Institute of Physics, pp. 2894–2896.

Ser. No. 8217411 Microbar Sensor (Patent Application—copy to be provided upon issuance of patent).

G.Y. Chen, et al., "Adsorption–induced surface stress and its effects on resonance frequency of microcantilevers", Journal of Applied Physics 77 (8), Apr. 15, 1995, American Institute of Physics, pp. 3618–3622.

*Primary Examiner*—Michael Brock
*Attorney, Agent, or Firm*—Joseph A. Marasco; Vincent A. Branton

[57] ABSTRACT

An improved microcantilever sensor is fabricated with at least one microcantilever attached to a piezoelectric transducer. The microcantilever is partially surface treated with a compound selective substance having substantially exclusive affinity for a targeted compound in a monitored atmosphere. The microcantilever sensor is also provided with a frequency detection means and a bending detection means. The frequency detection means is capable of detecting changes in the resonance frequency of the vibrated microcantilever in the monitored atmosphere. The bending detection means is capable of detecting changes in the bending of the vibrated microcantilever in the monitored atmosphere coactively with the frequency detection means. The piezoelectric transducer is excited by an oscillator means which provides a signal driving the transducer at a resonance frequency inducing a predetermined order of resonance on the partially treated microcantilever. Upon insertion into a monitored atmosphere, molecules of the targeted chemical attach to the treated regions of the microcantilever resulting in a change in oscillating mass as well as a change in microcantilever spring constant thereby influencing the resonant frequency of the microcantilever oscillation. Furthermore, the molecular attachment of the target chemical to the treated regions induce areas of mechanical strain in the microcantilever consistent with the treated regions thereby influencing microcantilever bending. The rate at which the treated microcantilever accumulates the target chemical is a function of the target chemical concentration. Consequently, the extent of microcantilever oscillation frequency change and bending is related to the concentration of target chemical within the monitored atmosphere.

32 Claims, 6 Drawing Sheets

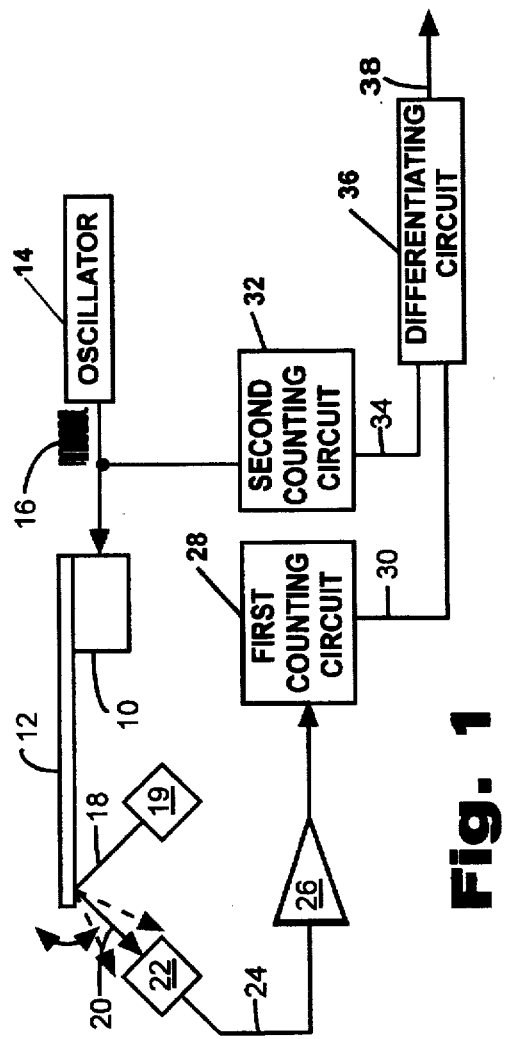
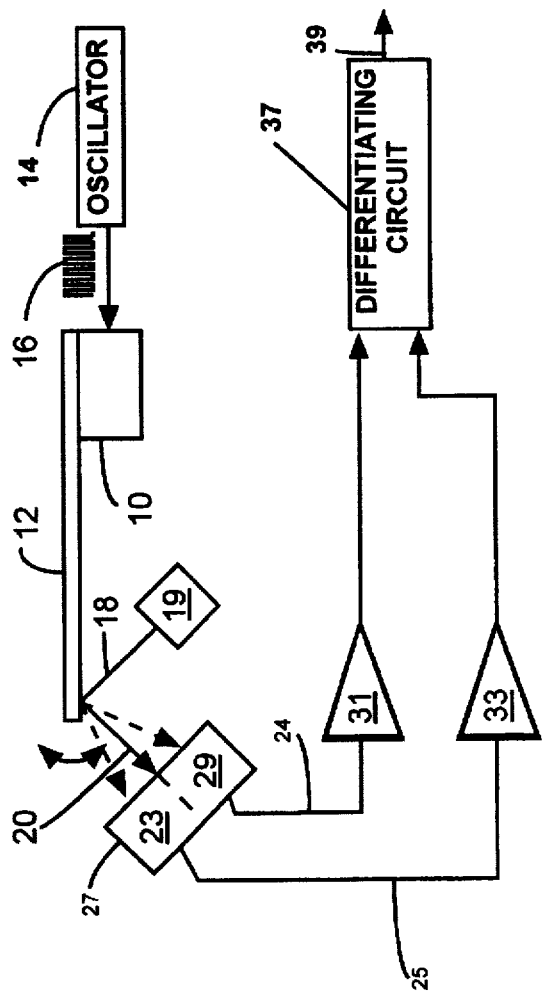
Fig. 1
Fig. 2

5,719,324

MICROCANTILEVER SENSOR

This invention was made with Government support under contract DE-AC05-84OR21400 awarded by the U.S. Department of Energy to Lockheed Martin Energy Systems, Inc. and the Government has certain rights in this invention.

FIELD OF THE INVENTION

The present invention relates to instruments for measuring the vapor concentration of a predetermined chemical or compound dispersed within a monitored atmosphere.

BACKGROUND

A pressing need exists in many industries, disciplines and governmental interests for a highly sensitive and selective chemical vapor detector. To qualify, such a detector must have such diverse characteristics as being small, rugged, inexpensive, selective, reversible and extremely sensitive.

The prior art is substantially represented by two sensor principles. One is the Surface Acoustic Wave (SAW) device and the other is the chemically sensitive Field Effect Transistor (Chem FET). Although these devices are reasonably inexpensive to produce, the respective sensitivity to the nanogram per $mm^2$ range is less than desired.

Spectroscopic approaches to this technical objective such as surface-enhanced Raman scattering (SERS) offer nanogram to picogram sensitivity but inherently require complex optical support and other equipment and all the consequential expense.

Chromatographic methods of vapor concentration measurement also require bulky, expensive, fragile hardware and specialized consumables.

OBJECTS OF THE INVENTION

Accordingly, it is an object of the present invention to teach the construction of a small, selective, inexpensive and highly sensitive vapor concentration detector.

It is another object of the invention to provide a vapor detection sensor that is sensitive in the sub-picogram range.

It is another object of the invention to provide a means for detecting the change in resonant frequency of a vibrating spring and interpreting the change in frequency as a indication of the presence of a desired vapor phase chemical.

It is another object of the invention to provide a means for detecting the bending of a vibrating spring and interpreting the bending as a indication of the presence of a desired vapor phase chemical.

It is another object of the invention to provide a means for detecting both the change in resonant frequency and the bending of a vibrating spring and interpreting both the change in frequency and the bending as a indication of the presence of a desired vapor phase chemical.

Further and other objects of the present invention will become apparent from the description contained herein.

SUMMARY OF THE INVENTION

In accordance with one aspect of the present invention, the foregoing and other objects are achieved by the exploitation of physical principles primarily comprising (a.) the relationship between resonant frequency and spring constant of an oscillating spring; and (b.) the relationship between sorption induced mechanical strain of an oscillating spring and the resultant bending of said spring.

An oscillator means provides an excitation signal to drive a piezoelectric vibrated microcantilever bar at a resonance frequency with a predetermined order of resonance. The piezoelectric vibrated microcantilever bar, which is the spring in this system, is treated to create regions having substantially exclusive affinity for the targeted compound. In some embodiments, the treated regions have an affinity for dissimilar vapor phase chemicals and sorptive properties. As the treated microcantilever element is vibrated in the monitored atmosphere, vapor phase molecules of the target compound attach to the treated regions of the microcantilever introducing sorption induced stresses to the microcantilever depending upon the relative treatment of the respective regions. The alteration of the microcantilever spring constant coupled with the change in microcantilever mass caused by sorption results in a related resonance frequency change. The mechanical strain established in the respective treated regions induces bending in the microcantilever. The change of frequency is independently measured by the reflected beam from a laser diode focused on and reflected from the microcantilever. The reflected laser beam is received by a photodiode detector serving as the signal source for a frequency counting circuit. The magnitude of the microcantilever frequency change is therefore proportional to the concentration of the targeted chemical or compound in the monitored atmosphere.

Additionally, the deflection, or bending, of the microcantilever element will vary in relation to sorption induced stresses. As the microcantilever element is vibrated in the monitored atmosphere, vapor phase molecules attach to the treated regions of the microcantilever thereby altering the mass loading and often inducing surface stresses to the microcantilever. The sorption induced stresses establish regions of differential mechanical strain consistent with the treated regions along the length of the microcantilever thereby inducing bending and a change in resonance frequency of the microcantilever. The bending magnitude and resonance frequency change are measured in a similar manner as the aforementioned method for independently measuring the resonance frequency change, however a center-crossing photodiode is employed for the detector. The resonance frequency change detection method and the bending detection method may be coupled to optimize detection of the overall microcantilever sensor assembly.

BRIEF DESCRIPTION OF THE DRAWINGS

In the drawing wherein like reference characters designate like or similar elements throughout the several figures of the drawings:

FIG. 1 is a pictorial schematic of the resonance frequency change detection invention assembly and mechanical operation.

FIG. 2 is a pictorial schematic of the bending detection invention assembly and mechanical operation.

FIG. 7b is a graph which illustrates the static bending represented by error voltage for the microcantilever having the characteristics shown in FIG. 7a.

Figure 3:
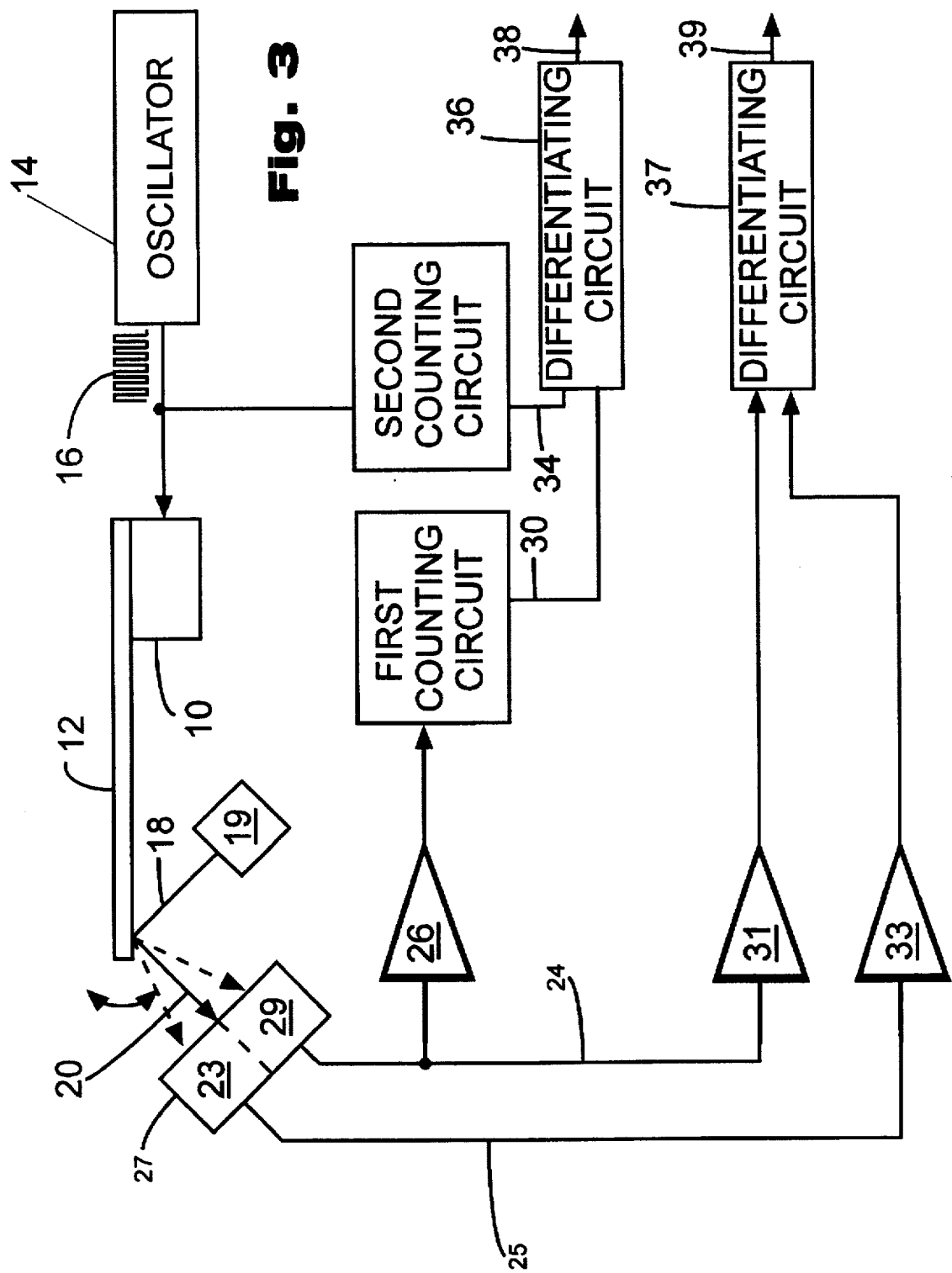
FIG. 3 is a pictorial schematic of the combination resonance frequency change detection and bending detection invention assembly and mechanical operation.

For a better understanding of the present invention, together with other and further objects, advantages and capabilities thereof, reference is made to the following disclosure and appended claims in connection with the above-described drawings.

DETAILED DESCRIPTION OF THE PREFERRED EMBODIMENTS

While there has been shown and described what is at present considered the preferred embodiments of the invention, it will be obvious to those skilled in the art that various changes and modifications can be made therein without departing from the scope of the invention defined by the appended claims.

FREQUENCY CHANGE EMBODIMENT

To illustrate the basic invention operating principles of the resonance frequency change detection embodiment, reference is given to FIG. 1 wherein element 10 represents a piezoelectric transducer supporting the attached end of a treated microcantilever 12 fabricated of quartz or silicon, for example. Responsive to a master oscillator 14 drive signal 16, the microcantilever is driven by the piezoelectric transducer at a non-loaded resonance frequency. A laser beam 18 emitted by laser diode 19 is reflected from the underside of microcantilever 12. The sweep of such reflection 20 is detected by an optical detector 22 such as a photodiode. As the reflected beam 20 sweeps back and forth across the detector 22, it produces a repetitive signal 24 with a frequency proportional to the oscillation frequency 16 of the microcantilever 12. Photodiode signal 24 is amplified 26 and the sweep pulses counted over a predetermined interval by a counting circuit 28. The interval count is the substance of signal 30 issued by counter 28. Simultaneously, the drive signal 16 is monitored by a second counting circuit 32 to produce the drive signal frequency count 34. The values of signals 30 and 34 are compared by a differentiating circuit 36 to produce a resultant signal 38.

The small differences between signals 30 and 34 are proportionally related to changes in the oscillating mass and spring constant of microcantilever 12 due to an accumulation of target chemicals or compounds on the microcantilever. Such accumulations are induced by the chemically selective treated regions of microcantilever 12. These chemically selective treated regions provide sensitivity and selectivity. Selectivity will depend on how uniquely a specific vapor or class of vapors interact with the treated regions.

BENDING DETECTION EMBODIMENT

To illustrate the basic invention operating principles of the bending detection embodiment, reference is given to FIG. 2 wherein the mode of fabrication, excitation and fabrication of the microcantilever is the same as discussed in the frequency change embodiment shown in FIG. 1. A laser beam 18 emitted by laser diode 19 is reflected from the underside of microcantilever 12. The sweep of such reflection 20 is detected by an optical detector 27 such as a displacement detector having a first cell 23 and a second cell 29, commonly known as a bicell. As the reflected beam 20 sweeps back and forth across the detector 27, it produces repetitive detection signals 24 and 29 each having a frequency proportional to the oscillation frequency 16 of the microcantilever 12 and a magnitude proportional to the extent of microcantilever 12 bending. Bicell detection signals 24 and 25 are amplified by linear amplifiers 31 and 33, respectively and subsequently compared by a differentiating circuit 37 to produce a resultant signal 39 which is linearly proportional to the bending of the microcantilever 12.

OPTIMIZED FREQUENCY/BENDING EMBODIMENT

To illustrate the basic invention operating principles of the optimized detection embodiment which combines the resonance frequency change and bending detection techniques, reference is given to FIG. 3 wherein the mode of fabrication, excitation and fabrication of the microcantilever is the same as discussed in FIG. 1 and FIG. 2. A laser beam 18 emitted by laser diode 19 is reflected from the underside of microcantilever 12. The sweep of such reflection 20 is detected by an optical detector 27 such as a displacement detector having a first cell 23 and a second cell 29, commonly known as a bicell. As the reflected beam 20 sweeps back and forth across the detector 27, it produces repetitive detection signals 24 and 25 each having a frequency proportional to the oscillation frequency 16 of the microcantilever 12 and a magnitude proportional to the extent of microcantilever 12 bending. Bicell detection signals 24 and 25 are amplified by linear amplifiers 31 and 33, respectively and subsequently compared by a differentiating circuit 37 to produce a resultant signal 39 which is linearly proportional to the bending of the microcantilever 12.

Additionally, detection signal 24 is amplified 26 and the sweep pulses counted over a predetermined interval by a counting circuit 28. The interval count is the substance of signal 30 issued by counter 28. Simultaneously, the drive signal 16 is monitored by a second counting circuit 32 to produce the drive signal frequency count 34. The values of signals 30 and 34 are compared by a differentiating circuit 36 to produce a resultant signal 38. Proportionalities of resultant signal 38 are as previously discussed.

USE OF SURFACE TREATMENTS

Sensitivity of each embodiment will depend on the total change in mass and change in spring constant due to the absorbed vapor, and thus on the responsiveness of the treated region as well as the treatment thickness. The response time of the system will be dependant upon the treatment thickness and the rate of gas diffusion into the treated region.

Any number of methods may be used to apply these selective treatments to the surface of the microcantilever including deposition from solutions using applicators such as microsyringes, Q-tips, brushes, and application by spin casting, dipping, air-brush spraying, Langmuir-Blodgett (L-B) fill transfer, plasma deposition, sputtering, evaporation, sublimation and self-assembled monlayers (SAMs).

Sorption can be reversible or irreversible based on treatment chemistry. A representative reversible example is: water absorbed into a gelatin film. A representative irreversible example is an amalgam of mercury on gold. If rapid response and recovery are desired, films which are only a few monolayers thick are preferred. Thicker films may be used to increase sensitivity or dynamic range.

MECHANICS OF ANALYTE/MICROCANTILEVER INTERACTION

The sorption induced stresses of the microcantilever establish regions of increased mechanical strain. The increased mechanical strain alters the spring constant of the microcantilever and creates a point of inflection experienced during microcantilever vibration at a resonance frequency. The harmonic order of resonance established in the microcantilever during use is affected by the location of this strain which is affected by the location of treated and nontreated regions on the microcantilever. The sorption induced stresses of the microcantilever establish regions of increased mechanical strain. The increased mechanical strain alters the spring constant of the microcantilever and creates a point of inflection experienced during microcantilever vibration at a resonance frequency.

For a microcantilever 12 having a density $\rho$, an area A, a Young's modulus E, and an area moment of Inertia I, the equation of motion for vibration perpendicular to the major axis (long axis) is given by:

$$EI \frac{\delta^4 z}{\delta y^4} + \rho A \frac{\delta^2 A}{\delta t^2} = 0 \qquad (1)$$

The frequency of vibration for the microcantilever 12, $\omega_n$ for the $n^{th}$ harmonic, is given by:

$$\omega_n = k_n^2 \sqrt{\frac{EI}{\rho A}} \quad n = 1, 2, 3 \ldots \qquad (2)$$

The values of $K_n l$ are:

$$K_n l = 1.875, 4.694, 7.855, \ldots \frac{(2n-1)}{2} \pi \qquad (3)$$

where K is the wave vector and l is the length of the microcantilever.

The moment of inertia I is given by:

$$I = \frac{wt^3}{12} \qquad (4)$$

where w is the width and t is the thickness of the beam. The beam can be approximated as a spring of a spring constant k:

$$k = \frac{Ewt^3}{4l^3} = \frac{3EI}{l^3} \qquad (5)$$

The resonance frequency of the microcantilevers is given by:

$$v = \frac{W}{2\pi} = \frac{1}{2\pi} \sqrt{\frac{k}{M^*}} \qquad (6)$$

where the effective mass $M^* = 0.24M$, where M is the mass of the microcantilever.

The above relationship illustrates that resonance is inversely proportional to the square root of the mass. Consequently, if a mass of material is added to the surface, the resonance frequency will change. For a uniformly deposited mass change, $\Delta m$, due to adsorption:

$$\Delta m = \frac{k}{4\pi^2 0.24} \left( \frac{1}{v_1^2} - \frac{1}{v_2^2} \right) \qquad (7)$$

where $v_1$ and $v_2$ are the resonance frequency before and after adsorption.

Additionally, the bending, of the microcantilever may change due to sorption induced differential stress. This stress may be large if the sorption on one region of the microcantilever varies with respect to another region. The microcantilever experiences bending under this differential stress, $\Delta s$:

$$\Delta s = s_1 - s_2 \qquad (8)$$

where $s_1$ and $s_2$ are the respective sorption induced stress on the top and bottom surfaces of the microcantilever.

The resultant bending, z, due to differential stress may be expressed:

$$z = \frac{3(1-v)l^2}{Et^2} \Delta s \qquad (9)$$

where t is the thickness, l is the length, v is the Poisson's ratio and E is the effective Young's modulus of the microcantilever.

In many cases differential stress alters the spring constant of the microcantilever thereby providing another source of change in resonance frequency. Hence, the change in microcantilever resonance frequency can be due to the combination of changes in mass loading and spring constant.

Often the resonance frequency of a microcantilever is given as stated in equation (6). However, upon introducing sorption induced surface stress, the spring constant k is expressed as:

$$k = k + \delta k \qquad (10)$$

where $\delta k$ is the surface contribution to the spring constant which may be expressed as:

$$\delta k = \frac{n^2}{4n} (s_1 + s_2) \qquad (11)$$

where $s_1$ and $s_2$ are the respective adsorption induced stresses on the top and bottom surfaces of the microcantilever and n is a proportionality constant.

The effective mass of the microcantilever, $M^*$, changes to:

$$M^* = M^* + 0.24 \delta M \qquad (12)$$

where $\delta M$ is the sorbed mass of the target chemical on the microcantilever treated region.

Substituting equations (10) and (12) into equation (6) yields resonance frequency $v_1$, representing the resonance frequency of the microcantilever due to the sorbed mass of the target chemical:

$$v_1 = \frac{1}{2\pi} \sqrt{\frac{k + \delta k}{M^* + 0.24 \delta M}} \qquad (13)$$

Since both k and M change due to sorption, the resonance frequency after sorption may be written as:

$$v_1 = v \left[ 1 + \frac{1}{2} \left( \frac{\delta k}{k} - \frac{\delta M}{M} \right) \right] \quad (14)$$

Figure 12A:
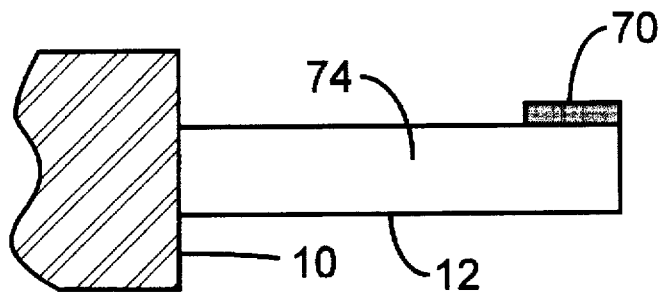
FIG. 12a is a representation of a microcantilever having a treated region located at the distal end of the microcantilever.
Figure 12B:
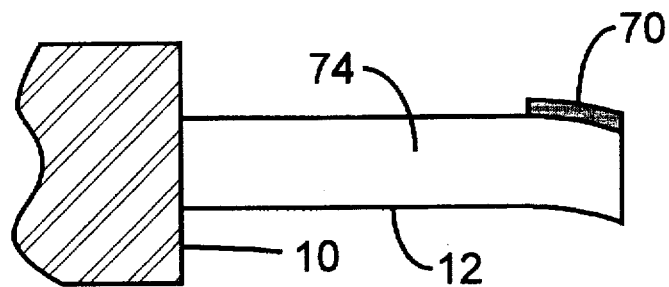
FIG. 12b is a representation of a microcantilever having a treated region located at the distal end of the microcantilever experiencing bending phenomena.
Figure 12C:
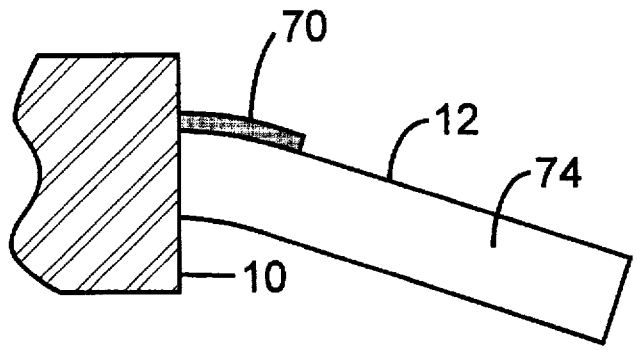
FIG. 12c is a representation of a microcantilever having a treated region located at the proximate end of the microcantilever experiencing bending phenomena.
Figure 12D:
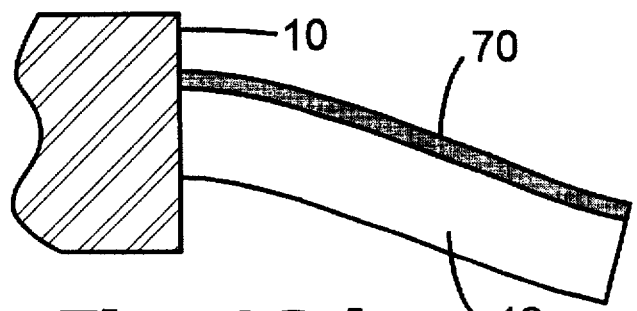
FIG. 12d is a representation of a microcantilever experiencing bending phenomena having a treated region over substantially the entire length thereof.

Therefore, as illustrated in FIGS. 12a, 12b, 12c and 12d, at least four distinct conditions can be observed due to sorption of molecules on a microcantilever where reference is given to equation 14 for the following discussion on the aforementioned conditions. In the first condition as shown in FIG. 12a, sorption induced alterations in spring constant are negligible and change in resonance frequency is due entirely to mass loading. In the second condition as shown in FIG. 12b, changes in both spring constant and mass loading are negligible. However, bending due to differential stresses established in the partially treated microcantilever is significant. Although the microcantilever deflects in this condition, there is little change in the observed resonance frequency. In the third condition as shown in FIG. 12c, sorption induced change in mass loading is negligible but the consequent change in spring constant significantly alters the resonance frequency. The fourth condition as shown in FIG. 12d combines the sorption induced changes in mass loading and spring constant in altering the resonance frequency of the microcantilever.

Figure 8:
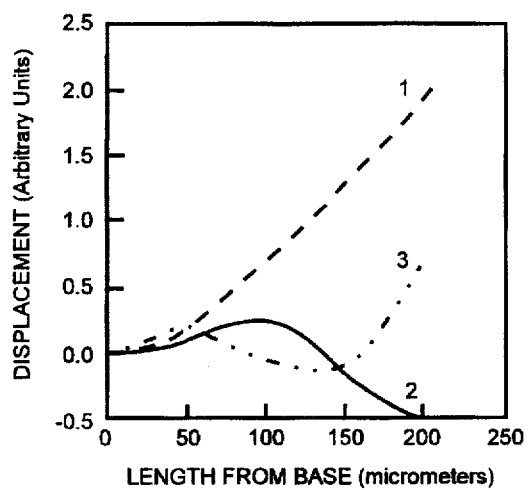
FIG. 8 is a graph which illustrates the displacement, or bending of a microcantilever having a length of 200 μm for the first three orders of resonance.

FIG. 8 shows the displacement of various points along the length of a microcantilever having a length of 200 μm for the first three orders of resonance, i.e., fundamental, second and third harmonics. For the first order resonance, maximum strain takes place at the base of the microcantilever where it increases rapidly from zero to a finite value. For second and third order resonances, changes in strain take place at different locations as indicated by the inflection points in the curves. As discussed above, sorption induced changes in stress can result in change in spring constant. If treated regions are placed on the microcantilever in regions of high strain, then sensitivity to sorption induced stress can be maximized. For example, sorption at the base of the microcantilever will exert a strong influence on first order resonance.

Figure 9:
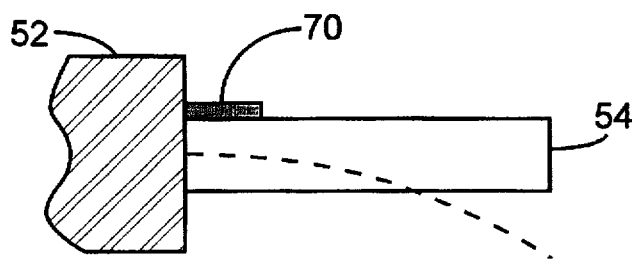
FIG. 9 is a representation of the invention as pertaining to a microcantilever for first order resonance.
Figure 10:
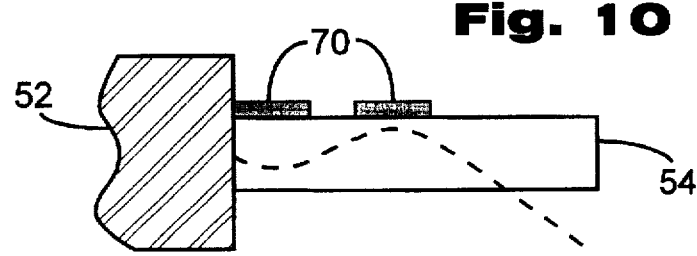
FIG. 10 is a representation of the invention as pertaining to a microcantilever for second order resonance.
Figure 11:
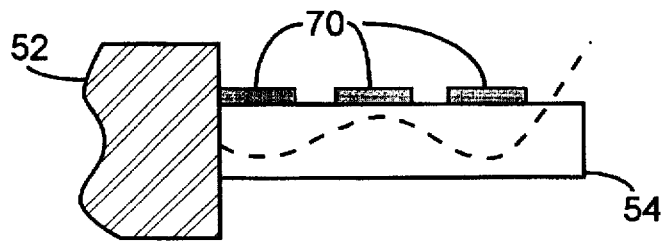
FIG. 11 is a representation of the invention as pertaining to a microcantilever for third order resonance.

FIGS. 9, 10 and 11 show three microcantilevers with adsorption sensitive areas specifically designed for sensitivity to the first three orders of resonance, respectively. FIG. 9 shows the preferred embodiment for a microcantilever optimized for response at the fundamental. FIG. 10 shows the preferred embodiment for a microcantilever optimized for response at the second harmonic. FIG. 11 shows the preferred embodiment for a microcantilever optimized for response at the third harmonic. Additionally, dissimilar compositions, each composition having an affinity for a different vapor phase molecule, may be implemented to treat the microcantilever. The dissimilar treatments may be positioned on the microcantilever at different points of inflection along the length of the microcantilever. The corresponding response at each treated area along the length of the microcantilever may then be monitored to identify the presence of several different vapor phase molecules with a single microcantilever.

EXAMPLE

Figure 7A:
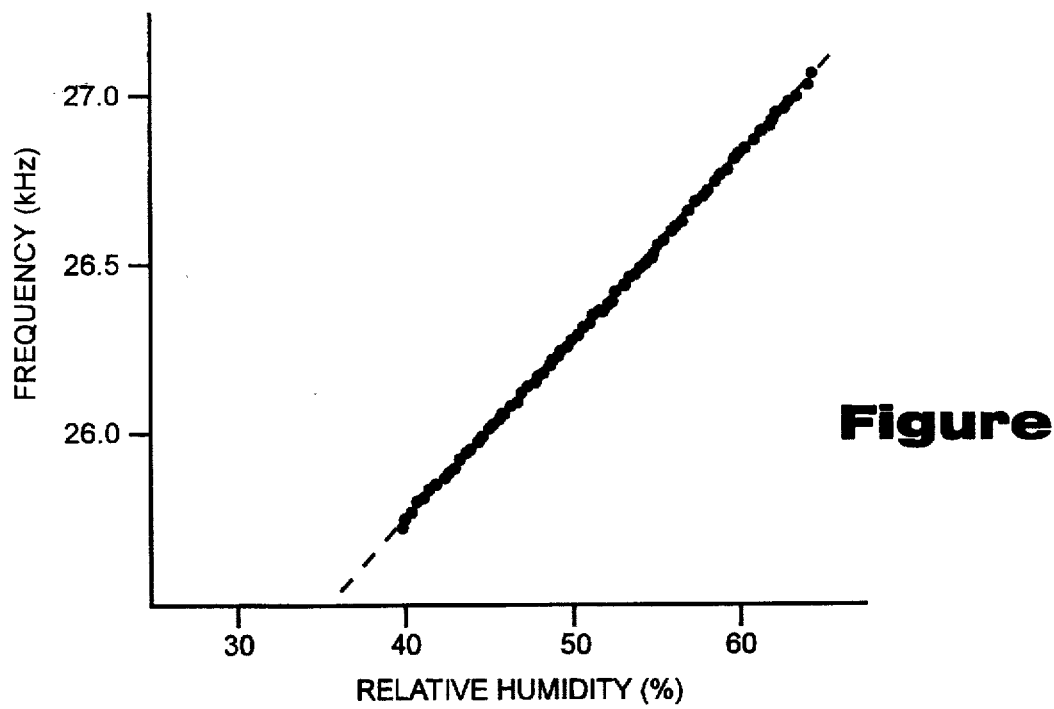
FIG. 7a is a graph which illustrates the microcantilever resonance frequency response as a function of the relative humidity of the monitored environment.
Figure 7B:
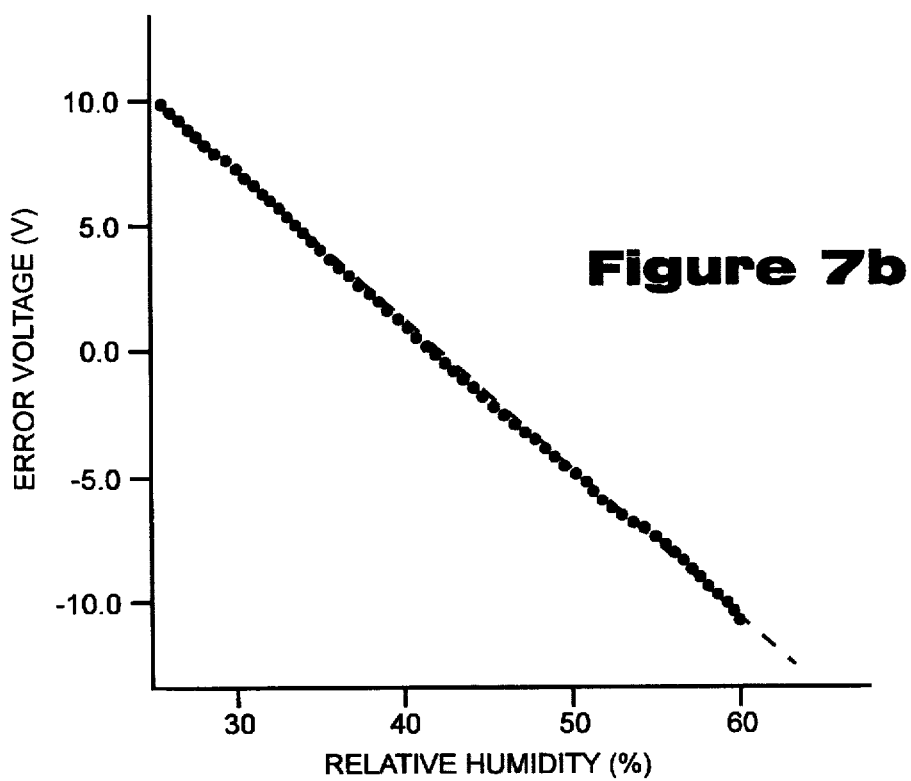

FIG. 7a shows the resonance frequency response for a silicon microcantilever treated with a gelatinous film. As the ambient humidity is increased, the effective spring constant increases thusly yielding a proportionate increase in resonance frequency. FIG. 7b shows the bending of the same microcantilever represented as error voltage. The variation in surface stress as a function of humidity produces changes in microcantilever bending proportionate to humidity.

MULTIPLEXED MICROCANTILEVERS

Figure 4:
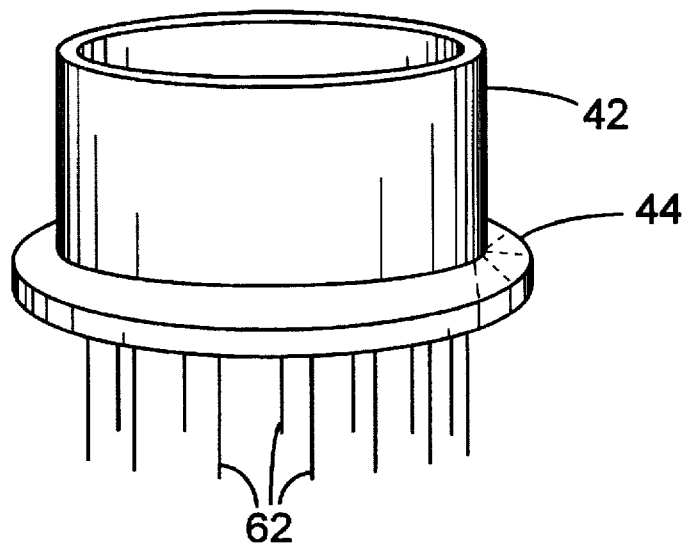
FIG. 4 is a pictorial representation of the assembled microcantilever sensor.
Figure 5:
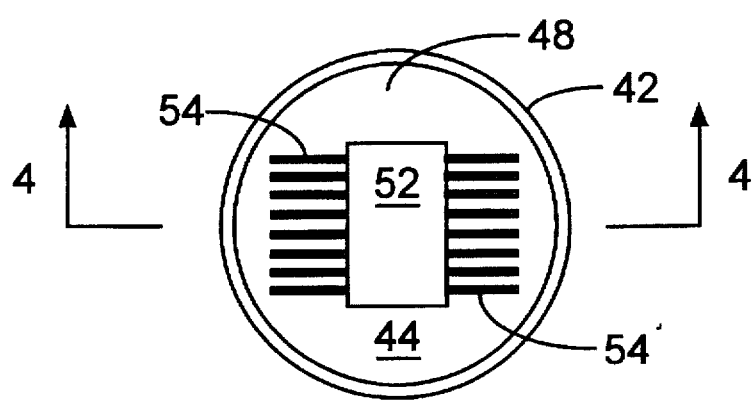
FIG. 5 is a top view of the cylindrical section of the assembled microcantilever sensor.
Figure 6:
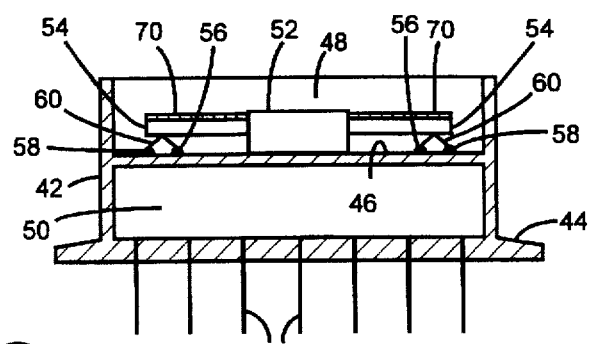
FIG. 6 is a cross section of the assembled microcantilever sensor along cut line 4 as shown in FIG. 5.

The invention embodiment illustrated in FIGS. 4, 5 and 6 is representative of a 16 sensor array of treated microcantilevers having treated regions 70, each microcantilever having different sorption characteristics with respect to the treated regions. Within an open ended cylinder 42 of 0.5 in. dia. by 0.5 in. height supported by a flanged base 44, a transverse partition 46 separates an outer, sensor volume 48 from a sealed, interior circuit volume 50. A single piezoelectric transducer 52 drives 16 microcantilevers 54. However, each microcantilever surface is distinctively treated as described herein.

Beneath the oscillating end of each microcantilever 54 is a laser diode 56 and optical detector 58 for respectively emitting and receiving laser beams 60 reflected from respective microcantilevers 54. Integrated microprocessor circuitry within the circuit volume 50 receives the raw optical detector 58 signals for development of respective, frequency and bending differential signals at leads, 62.

These several, distinctive signal leads 62 are connected with data processor terminals for preprogrammed analysis. Response patterns from several sensors are characteristic of the chemical or chemical combination present in the monitored vapor. Pattern recognition methods may be used for response to patterns that correspond to conditions of interest.

Another significant advantage of an array system is that it can easily identify a number of vapor conditions that is far in excess of the number of sensors in the array. Furthermore as new conditions arise, it is feasible to make the instrument responsive to them by changing only the pattern recognition software.

Another means for multiplexing the microcantilevers is to provide a microcantilever having several treated regions with each treated region having an affinity for a different vapor phase chemical. As sorption induced stresses and mass loading characteristics, consistant with the presence of a target chemical or group of chemicals, impact the resonance frequency of the microcantilever, the change in resonance frequency is independently detected at each of the treated regions along the microcantilever and respective detection signals are emitted. Each of the respective detection signals are compared with the drive oscillation signal to generate a differential signal proportional to the frequency difference between the drive oscillation signal and each of the respective detection signals. The differential signal is then related to a known spring constant corresponding to a known vapor phase chemical on each of the respective treated regions along the spring element.

ADDITIONAL EMBODIMENTS

From the foregoing disclosure, it will be appreciated that a microcantilever plate may be utilized in lieu of the microcantilevered bars 12 or 54 thereby raising the surface-to-volume ratio for greater sensitivity.

Additionally, sensor frequency and bending may be measured by means other than the photodetection method previously described. By one such other method, a silicon or GaAs microcantilever is fabricated with piezoresistive properties. The electrical resistance of the microcantilever changes under beam flexure. The resonant frequency and bending may be monitored as a microcantilever resistance signal.

Another sensor monitoring method relies upon capacitance synchronization using a parallel matched structure located a short distance from the moving structure.

Another sensor monitoring method relies upon electron tunneling between the cantilever and a fixed surface located a short distance from the moving structure.

Any of these alternative frequency and bending measuring methods would make the instrument more compact, durable, less expensive to manufacture and eliminate the need for separate optoelectric devices.

The above described sensor can be further modified to operate under liquid either by vibrating the microcantilever directly or by setting the microcantilever into oscillation by mechanically moving the liquid surrounding the microcantilever and observing the changes in frequency and bending corresponding to maximum amplitude of either characteristic.

While there has been shown and described what is at present considered the preferred embodiments of the invention, it will be obvious to those skilled in the art that various changes and modifications can be made therein without departing from the scope of the invention defined by the appended claims.

What is claimed is:

1. An apparatus for detecting the presence of a specific vapor phase chemical in a monitored atmosphere, comprising:
    a piezoelectric transducer having at least one cantilevered spring element secured thereto, said spring element having at least one treated region, said treated region treated with a chemical having an affinity for said specific vapor phase chemical; and
    oscillator means for stimulating said transducer at or about a resonant vibrational frequency of said cantilevered spring element; and
    detection means for measuring mechanical change in said spring element having a vibration detection means for measuring vibrational frequency change in said spring element due to a change in the spring constant of said spring element and a bending detection means for measuring the relative bending of said spring element due to mechanical stresses established in said treated regions of said spring element.

2. An apparatus for detecting the presence of a specific vapor phase chemical in a monitored atmosphere as described in claim 1 wherein said detection means comprises:
    vibration detection means for measuring vibrational frequency change in said spring element due to a change in the spring constant of said spring element; and
    bending detection means for measuring the relative bending of said spring element due to mechanical stresses established in said treated regions of said spring element,
    said vibration detection means comprising a laser diode for emitting a laser beam and a photodiode for detecting said laser beam, said laser diode being disposed to emit said laser beam against said vibrating spring element.

3. An apparatus as described by claim 2 wherein said photodiode is disposed for detecting a reflection of said laser beam from said spring element and emitting signals corresponding to the vibrational frequency and the bending magnitude of said spring element.

4. An apparatus as described in claim 1 wherein said vibration detection means comprises:
    a first counting circuit for measuring the transducer stimulation frequency of said oscillator means;
    a second counting circuit for measuring said spring element vibrational frequency; and
    a differentiating circuit for determining a frequency differential between said stimulation frequency and said spring element vibrational frequency.

5. An apparatus as described in claim 1 wherein said bending detection means comprises:
    a photodetector capable of providing a first and second output signal corresponding to the bending magnitude of said spring element;
    a first amplification circuit for amplifying said first output signal of said bending detection means;
    a second amplification circuit for amplifying said second output signal of said bending detection means; and
    a differentiating circuit for determining a magnitude differential between said first and second output signals.

6. An apparatus as described in claim 1 wherein said detection means further comprises a mass variation detection means for measuring the change in oscillating mass of said spring element due to absorbtion of said vapor-phase chemical from said atmosphere on said treated region.

7. A method for detecting the presence of a specific vapor phase chemical in a monitored atmosphere comprising the steps of:
    fabricating a cantilever spring element having a surface and a structural base secured to a piezoelectric transducer;
    treating a surface of said spring element with at least one chemical having an affinity for said predetermined vapor phase chemical;
    electrically driving said transducer at or near a resonance frequency of said spring element;
    exposing said treated and driven cantilever spring element in a monitored atmosphere;
    measuring changes in a set of mechanical parameters said mechanical parameters comprising vibrational frequency change and bending of said cantilever spring element over a predetermined time period in said monitored atmosphere; and
    relating said mechanical parameter changes to a concentration value of said specific vapor phase chemical in said monitored atmosphere.

8. A method for detecting the presence of a specific vapor phase chemical in a monitored atmosphere as described in claim 7 wherein said set of mechanical parameters comprises vibrational frequency change and bending of said cantilever spring element, and
    wherein a first signal that is proportional to the vibrational frequency of said spring element is generated by the reflection of a laser beam from said surface of said spring element.

9. A method as described in claim 8 wherein first and second bending signals which are proportional to the bending magnitude of said spring element are generated by the reflection of a laser beam from said surface of said spring element.

10. A method as described by claim 9 wherein said first and second bending signals are generated by a photodiode in response to a cyclic stimulation from said laser beam.

11. A method as described in claim 10 wherein said laser beam is generated by a laser diode.

12. A method as described in claim 11 wherein said first and second bending signals are compared to generate a differential signal proportional to the bending magnitude difference between said first and second bending signals.

13. A method as described by claim 12 wherein said differential signal is related to a known bending magnitude corresponding to said specific vapor phase chemical on said treated region of said spring element.

14. A method as described by claim 8 wherein said first signal is generated by a photodiode in response to a cyclic stimulation from said reflected laser beam.

15. A method as described in claim 14 wherein said laser beam is generated by a laser diode.

16. A method as described in claim 15 wherein a second signal is generated that is proportional to the driving frequency of said transducer.

17. A method as described in claim 16 wherein said first and second signals are compared to generate a differential signal proportional to the frequency difference between said first and second signals.

18. A method as described by claim 17 wherein said differential signal is related to a known spring constant corresponding to said specific vapor phase chemical on said treated region of said spring element.

19. A method as described by claim 8 wherein said spring element comprises a plurality of treated regions, each of said regions having an affinity for a dissimilar predetermined vapor phase chemical.

20. A method as described by claim 19 wherein each of said plurality of treated regions is located on said spring element at a position corresponding to a point of inflection associated with a harmonic established by said resonance frequency.

21. A method as described in claim 20 wherein the change in resonance frequency is independently detected at each of said treated regions along said spring element and respective detection signals are emitted.

22. A method as described in claim 21 wherein each of said each of said respective signals are compared with said first signal to generate differential signals proportional to the frequency difference between said first signal and each of said respective signals.

23. A method as described in claim 22 wherein said differential signal is related to a known spring constant corresponding to a known vapor phase chemical on each of said respective treated regions along said spring element.

24. A method as described by claim 8 wherein said transducer vibrates a plurality of spring elements.

25. A method as described in claim 24 wherein each of said plurality of spring elements is provided with a distinctive treated region having affinity for a respectively distinctive vapor phase chemical.

26. A method as described in claim 25 wherein the vibrational frequency of each of said plurality of spring elements is independently measured.

27. A method as described in claim 26 wherein first signals proportional to each of said independent frequency measurements are directed to a microprocessor for preprogrammed pattern recognition analysis.

28. A method as described by claim 9 wherein said transducer vibrates a plurality of spring elements.

29. A method as described in claim 28 wherein each of said plurality of spring elements is provided with a distinctive treated region having affinity for a respectively distinctive vapor phase chemical.

30. A method as described in claim 29 wherein the bending magnitude of each of said plurality of spring elements is independently measured.

31. A method as described in claim 30 wherein first and second bending signals proportional to each of said independent bending measurements are directed to a microprocessor for preprogrammed pattern recognition analysis.

32. A method as described in claim 7 wherein said mechanical parameters further comprise change in oscillating mass of said spring element.

\* \* \* \* \*